United States Patent
Fitzgibbons et al.

(10) Patent No.: US 11,950,848 B2
(45) Date of Patent: Apr. 9, 2024

(54) FUNDUS IMAGING FOR MICROVASCULAR ASSESSMENT

(71) Applicant: Welch Allyn, Inc., Skaneateles Falls, NY (US)

(72) Inventors: Stacey A. Fitzgibbons, Dewitt, NY (US); Allen R. Hart, Knoxville, TN (US); David L. Ribble, Indianapolis, IN (US); Craig M. Meyerson, Syracuse, NY (US); Heather Whitt, Kirkville, NY (US); Gene J. Wolfe, Pittsford, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 380 days.

(21) Appl. No.: 17/386,173

(22) Filed: Jul. 27, 2021

(65) Prior Publication Data

US 2022/0039652 A1 Feb. 10, 2022

Related U.S. Application Data

(60) Provisional application No. 63/063,619, filed on Aug. 10, 2020.

(51) Int. Cl.
*A61B 3/10* (2006.01)
*A61B 3/02* (2006.01)
(Continued)

(52) U.S. Cl.
CPC ............ *A61B 3/1241* (2013.01); *A61B 3/112* (2013.01); *A61B 3/14* (2013.01); *A61B 5/0013* (2013.01)

(58) Field of Classification Search
CPC ......... A61B 3/02; A61B 3/102; A61B 3/1025; A61B 3/1015; A61B 3/1225; A61B 3/024;
(Continued)

(56) References Cited

U.S. PATENT DOCUMENTS 5,279,298 A 1/1994 Flower
9,237,846 B2 1/2016 Mowrey et al.
(Continued)

FOREIGN PATENT DOCUMENTS

CN 110448267 A 11/2019

OTHER PUBLICATIONS

Simkiene Jurate et al., "Alterations of retinal vessels in patients with sepsis," https://link.springer.com/article/10.1007/s10877-019-00401-0, Journal of Clinical Monitoring and Computing (2020), Published online: Oct. 24, 2019, 6 pages.
(Continued)

*Primary Examiner* — Dawayne Pinkney
(74) *Attorney, Agent, or Firm* — Merchant & Gould P.C.

(57) ABSTRACT

An example system for microvascular assessment of a patient can include: a fundus imaging device including: a camera configured to capture one or more images of an eye of the patient; and at least one light source; and a microvascular assessment computing device including: a processor; and memory encoding instructions which, when executed by the processor, cause the system to: activate the light source to direct light at a fundus of the eye of the patient; capture, with the camera, one or more images of the fundus of the patient, the fundus comprising a plurality of blood vessels; and analyze with the microvascular assessment computing device, the one or more images to determine a microvasculature health index for the patient.

6 Claims, 13 Drawing Sheets

(51) Int. Cl.
*A61B 3/11* (2006.01)
*A61B 3/12* (2006.01)
*A61B 3/14* (2006.01)
*A61B 5/00* (2006.01)

(58) Field of Classification Search
CPC ..... A61B 5/0205; A61B 5/021; A61B 5/7264; A61B 5/7275; A61B 5/746; A61B 5/02405; A61B 5/0816; A61B 5/14551; A61B 5/412; A61B 5/6833; A61B 5/6892; G16H 15/00; G16H 10/60; G16H 40/20; G16H 40/63; G16H 40/67; G16H 50/20; G16H 50/30; G16H 50/50
USPC ........ 351/200, 205, 206, 210, 221–223, 246
See application file for complete search history.

(56) References Cited

U.S. PATENT DOCUMENTS

| | | | |
|---|---|---|---|
| 10,993,613 B2 | 5/2021 | Hart et al. | |
| 11,589,852 B2* | 2/2023 | Chaturvedi | A61B 5/0082 |
| 2004/0064057 A1 | 4/2004 | Siegel | |
| 2004/0258285 A1* | 12/2004 | Hansen | G06T 7/0012 382/128 |
| 2006/0077348 A1 | 4/2006 | Gorin | |
| 2009/0153797 A1* | 6/2009 | Allon | A61B 3/12 362/11 |
| 2014/0313482 A1 | 10/2014 | Shahidi et al. | |
| 2014/0314288 A1* | 10/2014 | Roychowdhury | G06T 7/0012 382/128 |
| 2017/0100029 A1 | 4/2017 | Faber | |
| 2018/0140180 A1* | 5/2018 | Coleman | G06V 40/197 |
| 2019/0357769 A1 | 11/2019 | Wang | |
| 2020/0196861 A1 | 6/2020 | Hart et al. | |
| 2020/0202529 A1 | 6/2020 | Hart et al. | |
| 2020/0204710 A1 | 6/2020 | Myers et al. | |
| 2020/0305783 A1 | 10/2020 | Baker et al. | |
| 2020/0335190 A1 | 10/2020 | Chung et al. | |
| 2021/0059597 A1 | 3/2021 | Chung et al. | |

OTHER PUBLICATIONS

Simkiene Jurate et al., "Ocular microvascular changes in patients with sepsis: a prospective observational study," https://www.ncbi.nlm.nih.gov/pmc/articles/PMC7138894/, Department of Intensive Care Medicine, Lithuanian University of Health Sciences, Simkien et al. Ann. Intensive Care (2020), 9 pages.
Tan Bingyao, PhD. et al., "Quantitative Microvascular Analysis with Wide-Field Optical Coherence Tomography Angiography in Eyes with Diabetic Retinopathy," https://jamanetwork.com/journals/jamanetworkopen/fullarticle/2758862, JAMA Network Open | Ophthalmology Jan. 17, 2020, 13 pages.
U.S. Appl. No. 63/063,593, filed Aug. 10, 2020.
U.S. Appl. No. 63/063,619, filed Aug. 10, 2020.
Extended European Search Report for Application No. 21189947.1 dated Jan. 5, 2022.

* cited by examiner

FUNDUS IMAGING FOR MICROVASCULAR ASSESSMENT

BACKGROUND

It is often observed that certain patients diagnosed with a disease have mild symptoms at the onset of the disease, but then experience a rapid deterioration. For example, patients diagnosed with sepsis or coronavirus disease can have mild symptoms that later lead to acute respiratory distress, multiple-organ failure, septic shock, and blood clots.

In patients diagnosed with sepsis or coronavirus disease, endothelial cell malfunction may occur, causing microvascular problems and rapid deterioration of the patient's condition. Changes in the microvasculature may precede changes to macro vital signs such as heart rate, respiration rate, and blood pressure, and can be helpful to predict patient deterioration.

SUMMARY

Embodiments of the disclosure are directed to microvascular assessment of a patient using a fundus imaging device.

The details of one or more techniques are set forth in the accompanying drawings and the description below. Other features, objects, and advantages of these techniques will be apparent from the description, drawings, and claims.

DETAILED DESCRIPTION

Microvascular evaluation of a subject is critical for diagnosis and monitoring of a number of critical and emergent conditions including Sepsis. The endothelial cell dysfunction is well demonstrated in its effect upon microvascular structure, function and, most importantly, appearance. There is great difficulty in localizing and imaging such tissue beds in the body. Sublingual, nail fold and other areas have been explored, however a very rich source of dense vascular structures exist in the eye. The retina is a very dense bed of vascular content.

Fundus imaging is optimized to provide a good image representing the conditions of the retina, optic nerve, optic disc, cup, and other areas. Additionally, in order to obtain good dynamic contrast and accurate color reproduction typically fundus imaging is done using a high intensity flash of neutral white light. This has the deleterious effect of causing the pupil to contract, limiting the field of view available. This also limits the ability to continuously image the vasculature without dilation or patient discomfort.

The present disclosure is directed to methods and systems for assessing microvascular health of a patient using a fundus imaging device. As used herein, "fundus" refers to the eye fundus and includes the retina, optic nerve, macula, vitreous, choroid, and posterior pole. In some embodiments, the fundus imaging device is modified to improve its capabilities for direct evaluation of endothelial cell dysfunction in a patient.

Figure 1:
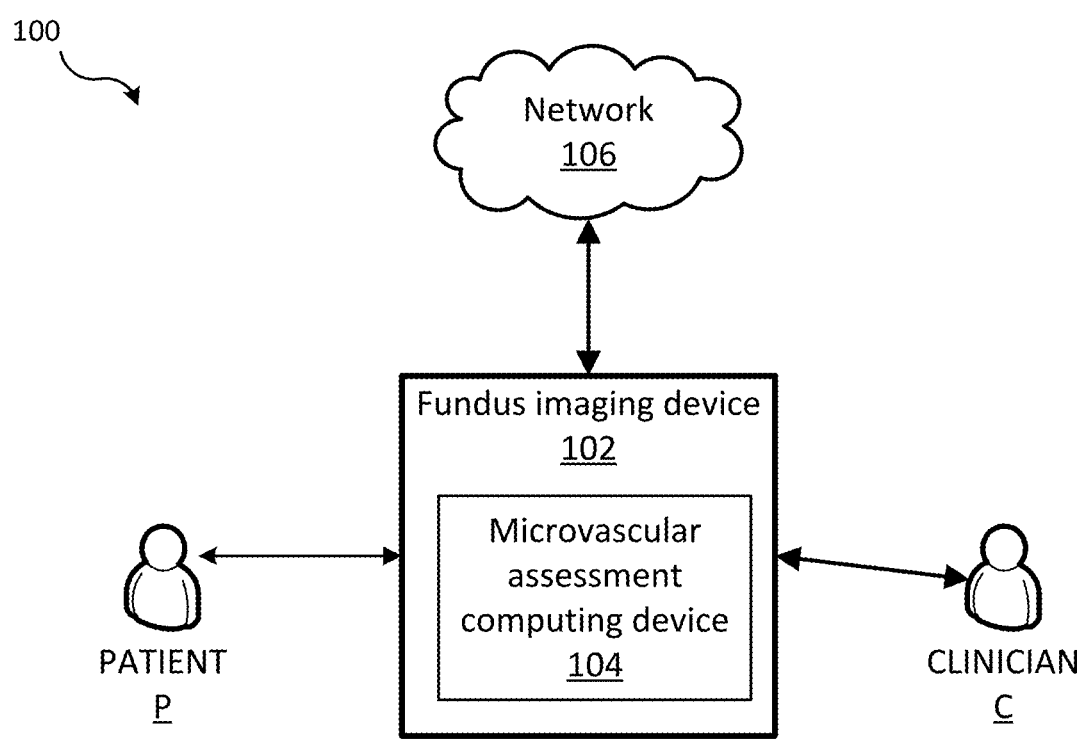
FIG. 1 is a schematic diagram illustrating an example system for microvascular assessment of a patient.

FIG. 1 is a schematic diagram illustrating an example system 100 for microvascular assessment of a patient. Similar systems are described in U.S. patent application Ser. No. 16/443,234 filed on Jun. 17, 2019, U.S. patent application Ser. No. 16/229,939 filed on Dec. 21, 2018, and U.S. patent application Ser. No. 16/230,315 filed on Dec. 21, 2018, all of which are hereby incorporated by reference in their entireties. The system 100 includes a fundus imaging device 102 including a microvascular assessment computing device 104 in communication with a network 106.

A clinician C operates the fundus imaging device 102 to capture images of an eye of a patient P. In some embodiments, the fundus imaging device 102 operates to capture one or more images of a fundus. In some embodiments, the fundus imaging device 102 operates to capture a series of images of the patient P's pupil. In some embodiments, the fundus imaging device 102 operates to capture one or more images of blood vessels, including microvessels, visible on the patient P's fundus. As shown in FIG. 1, the fundus imaging device 102 includes a microvascular assessment computing device 104. However, the microvascular assessment computing device 104 could be housed on a remote server in communication with the fundus imaging device 102 via the network 106.

The microvascular assessment computing device 104 operates to analyze images captured by the fundus imaging device 102. The images are analyzed to assess the microvasculature of the patient P. The assessment can be utilized by the clinician C to make a determination about a clinical condition of the patient P.

The example fundus imaging device 102 is connected to a network 106. The network 106 may include any type of wireless network, a wired network, or any communication network known in the art. For example, wireless connections can include cellular network connections and connections made using protocols such as 802.11a, b, and/or g. In other examples, a wireless connection can be accomplished directly between the fundus imaging device 102 and an external display using one or more wired or wireless protocols, such as Bluetooth, Wi-Fi Direct, radio-frequency identification (RFID), or Zigbee. Other configurations are possible.

The system 100 can be used to assist the clinician C in screening for, monitoring, or diagnosing various eye diseases, such as hypertension, diabetic retinopathy, glaucoma and papilledema. The system 100 can also be used to assist the clinician C in screening for signs of endothelial deterioration, which is an early indication of various health conditions such as sepsis. It will be appreciated that the clinician C that operates the fundus imaging system 102 can be different from the clinician C evaluating the resulting image.

Figure 2:
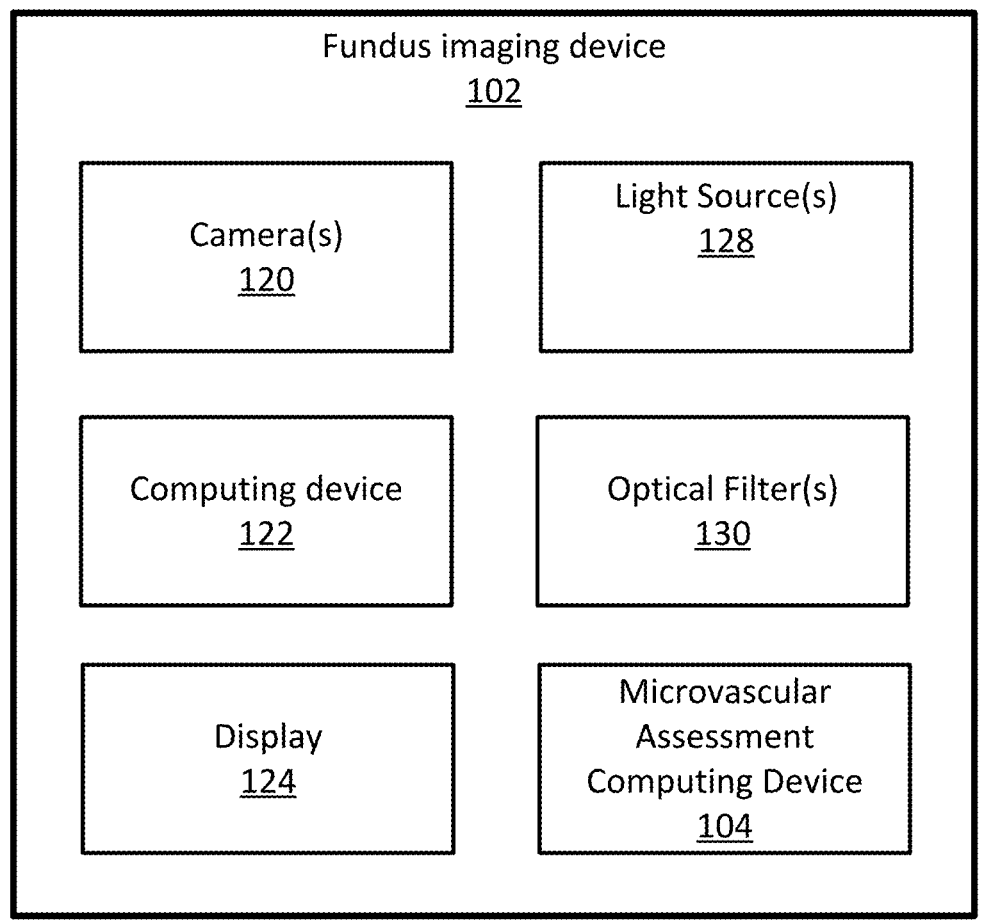
FIG. 2 is a block diagram providing a detailed schematic illustration of the fundus imaging device of FIG. 1.

FIG. 2 is a block diagram providing a detailed schematic illustration of the fundus imaging device 102 of FIG. 1. In this example, the fundus imaging device 102 includes a camera 120, a computing device 122, a display 124, a light source 128, an optical filter 130, and the microvascular assessment computing device. In some embodiments, the fundus imaging device 102 can include fewer or greater components depending on the particular intended use of the fundus imaging device 102.

The camera 120 operates to record images of a patient's eyes. In some embodiments, the camera 120 is a digital camera including a lens, an aperture, and a sensor array. In some embodiments, the camera 120 lens is a variable focus lens, such as a lens moved by a step motor, or a fluid lens, also known as a liquid lens in the art. In some embodiments, the camera 120 is configured to record images of the fundus one eye at a time. In other embodiments, the camera 120 is configured to record an image of both eyes substantially simultaneously. In those embodiments, the fundus imaging device 102 can include two separate cameras 120, one for each eye.

The computing device 122 operates to execute software programs and access data. The computing device 122 includes at least a processor and memory. The computing device 122 regulates the operation of the camera 120, display 124, and other components of the fundus imaging device 102. The computing device 122 also mediates communication through the network 106. A more detailed view of an example computing device 122 is provided in FIG. 13.

The display 124 operates to provide visual output to a clinician C operating the fundus imaging device 102. In some embodiments, the housing supports the display 124. The display 124 functions to reproduce the images produced by the fundus imaging device 102 in a size and format readable by the clinician C. For example, the display 124 can be a liquid crystal display (LCD) and active matrix organic light emitting diode (AMOLED) display. The display can be touch sensitive.

The light source 128 operates to direct light at the patient's eye. In some embodiments, the light source 128 is an infrared LED. In some embodiments, the light source 128 is a visible light LED. In some embodiments, the light source 128 includes both infrared and visible light LEDs. In some embodiments, the light source 128 is configured to provide continuous light. In some embodiments, the light source 128 is configured to provide a brief flash of light.

The optical filter 130 operates to selectively transmit light in a particular range of wavelengths. In some embodiments, the optical filter 130 is a bandpass filter configured to filter out all wavelengths of light except for a particular range of wavelengths. In some embodiments, the bandpass filter is configured to only allow yellow or green light to pass through. In some embodiments, the optical filter 130 is a polarizing filter configured to allow light waves of a specific polarization to pass through while blocking light waves of other polarizations.

In some embodiments, a phase adjustable linear polarizer is provided both at an illumination source and at an image return path of the fundus imaging device 102. In general, polarization can be used to manage reflections and suppress glare from linear artifacts in an imaging system. This is used here to enhance the linear appearance of the microvasculature at several targeted vessel locations. Images are continuously acquired of the microvasculature. The polarizers are gradually rotated through about a 90 degree range during image acquisition. An image differencing algorithm is employed designed to extract the image at the optimal polarization angle.

Figure 3:
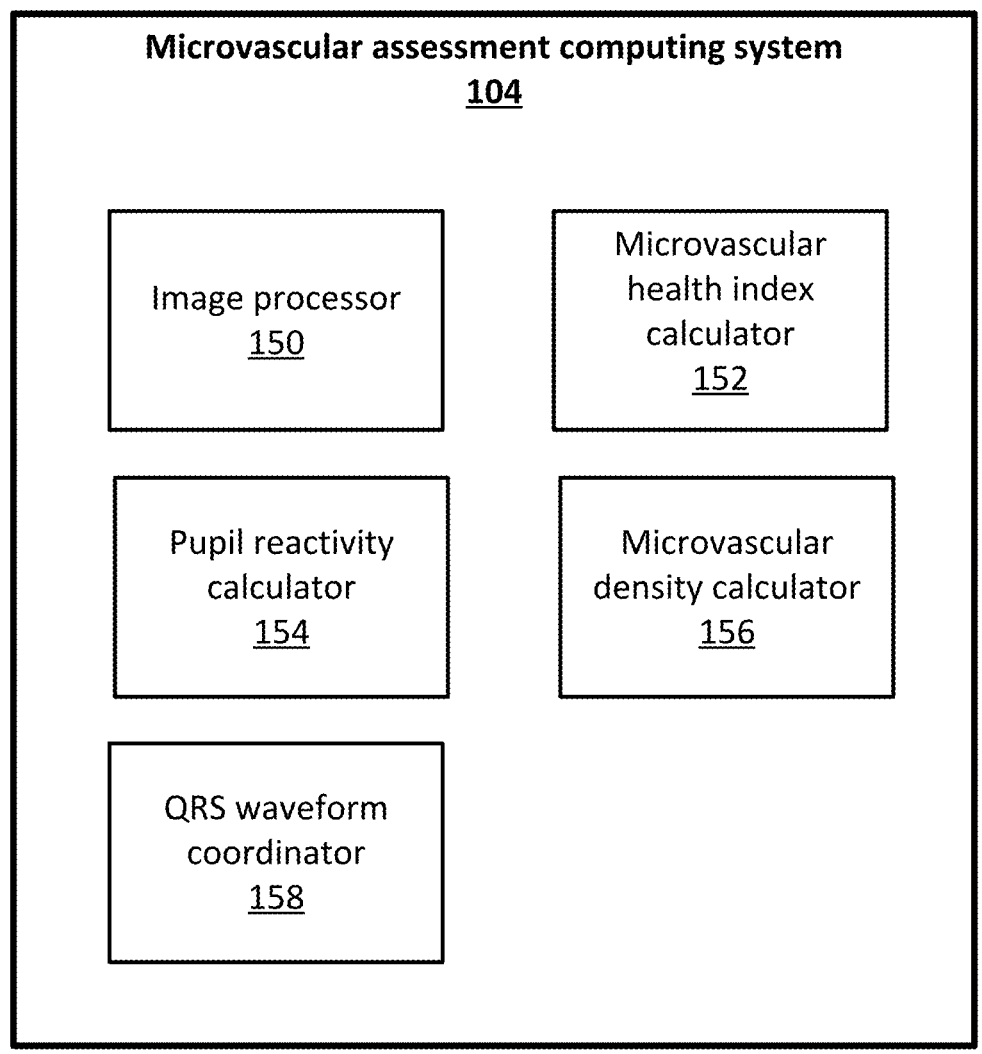
FIG. 3 is a block diagram providing a detailed schematic illustration of the microvascular assessment computing device of FIG. 1.
Figure 4:
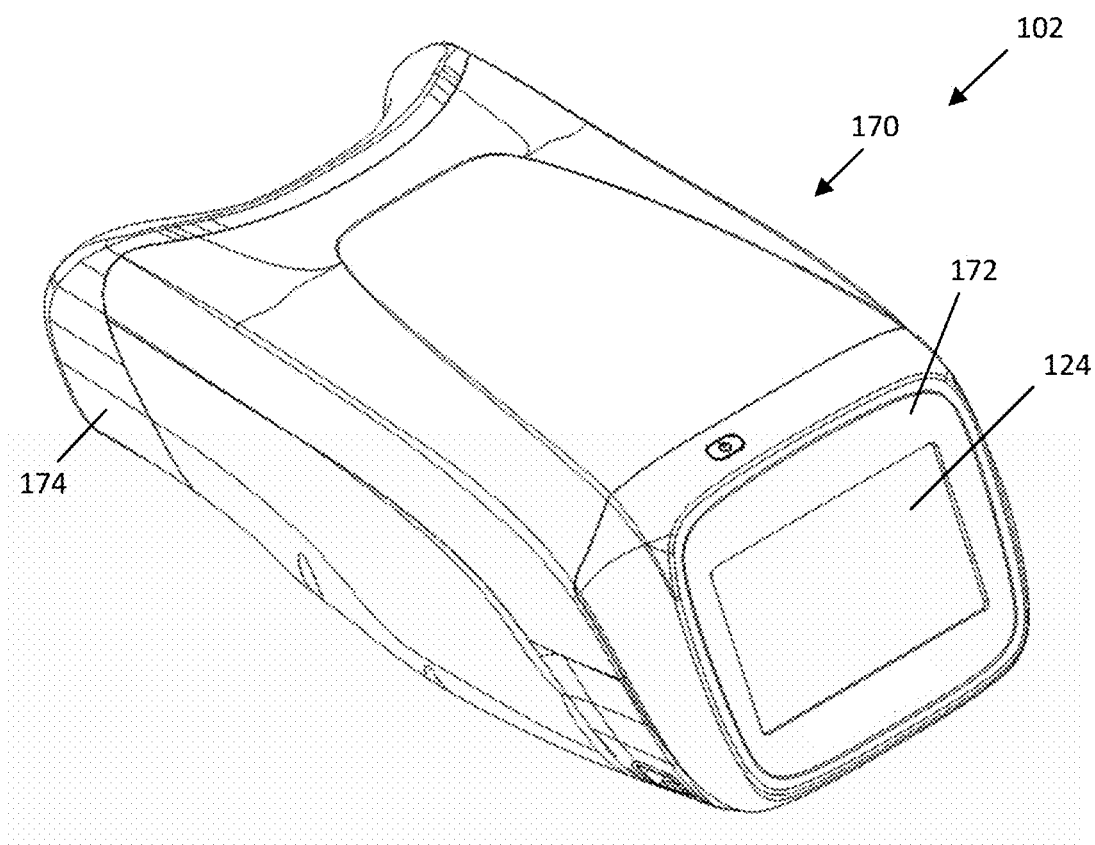
FIG. 4 is an embodiment of the example fundus imaging device of FIG. 1.

FIG. 3 is a block diagram providing a detailed schematic illustration of the microvascular assessment computing device 104 of FIGS. 1 and 2. In this example, the microvascular assessment computing device 104 includes an image processor 150, a microvascular health index calculator 152, a pupil reactivity calculator 154, a microvascular density calculator 156, and a QRS waveform coordinator 158.

The image processor 150 operates to manipulate and modify images received from the fundus imaging device 102. Such manipulations are used to enhance different aspects of the images to make it easier to detect various parameters of the blood vessels.

The microvascular health index calculator 152 operates to determine a microvascular health index of a patient based on analysis of one or more images captured by the fundus imaging device 102. In some embodiments, the images are manipulated and modified by the image processor 150 before being analyzed. In some embodiments, other components of the microvascular assessment computing device 104 such as the pupil reactivity calculator 154 or the microvascular density calculator 156 operate in conjunction with the microvascular health index calculator 152 to determine a clinical condition of the patient. Inferences about the overall endothelial health of the patient can be determined based on various measurements of the patient's eyes. In some embodiments, the microvascular health index is based on a comparison with other patients having similar demographics to the patient being examined.

The pupil reactivity calculator 154 operates to measure the diameter of a patient's pupil over time as it responds to light stimuli. The reactivity is based on: 1) how quickly the pupil closed or opened, 2) how far the pupil closed or opened, and 3) how long the pupil stayed closed or opened.

Figure 10:
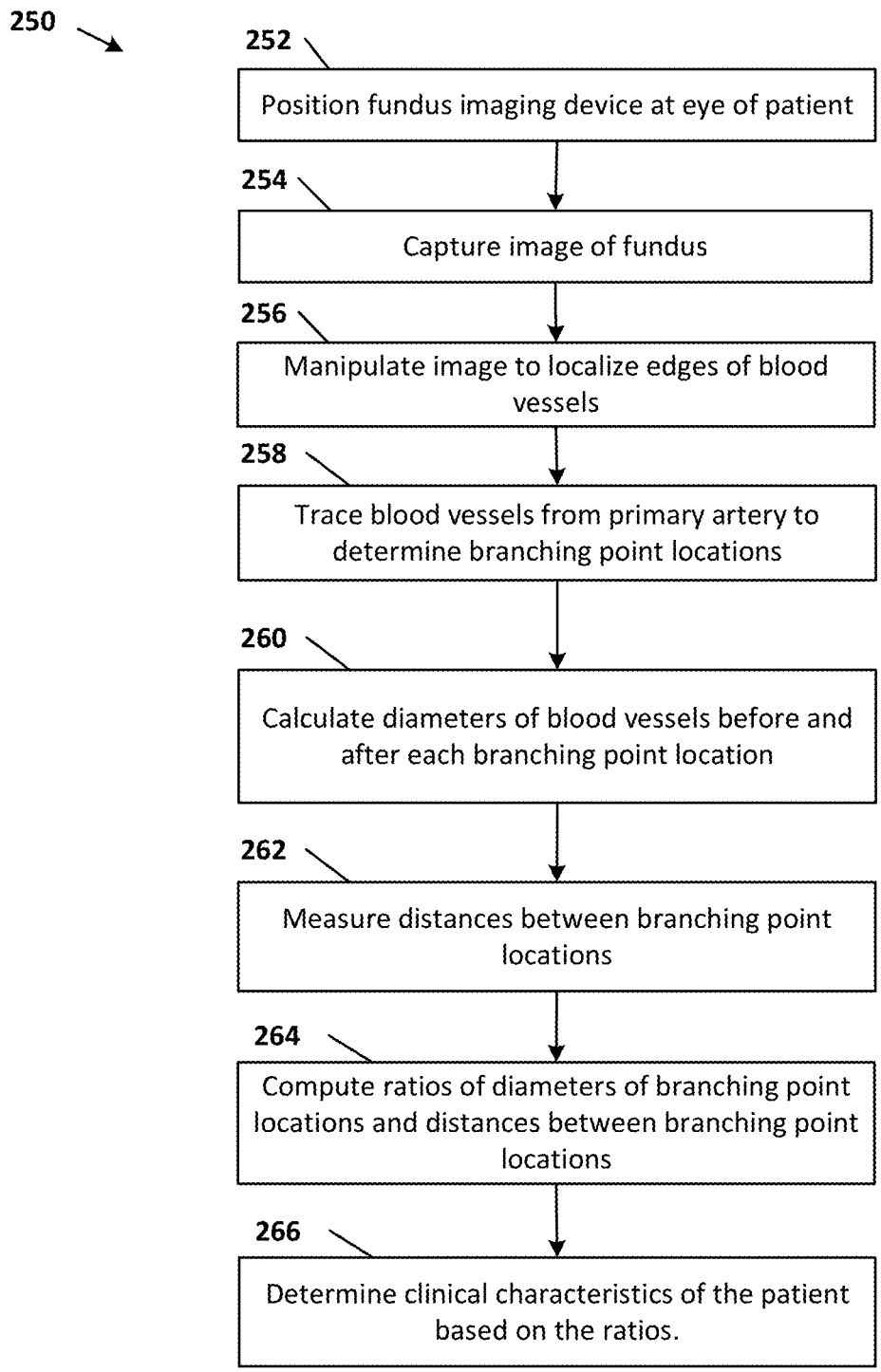
FIG. 10 is a flow diagram of another example method of assessing microvasculature of a patient.

The microvascular density calculator 156 operates to measure a ratio of diameters and distances of branching locations as described in FIG. 10.

The QRS waveform coordinator 158 operates to receive ECG data from an ECG machine. The QRS waveform of several heartbeats is used to time the analysis of images captured of the fundus, as described further below.

FIGS. 4-7 show an example of the fundus imaging device 102 that includes a housing 170 that supports the components of the device. The housing 170 supports the display 124 at a first end 172 and is configured to engage one or both eyes of the patient P at an opposite end 174. As will be described herein, the fundus imaging device 102 can be used to implement one or more of the described methods for imaging of the fundus and microvasculature therein.

Figure 5:
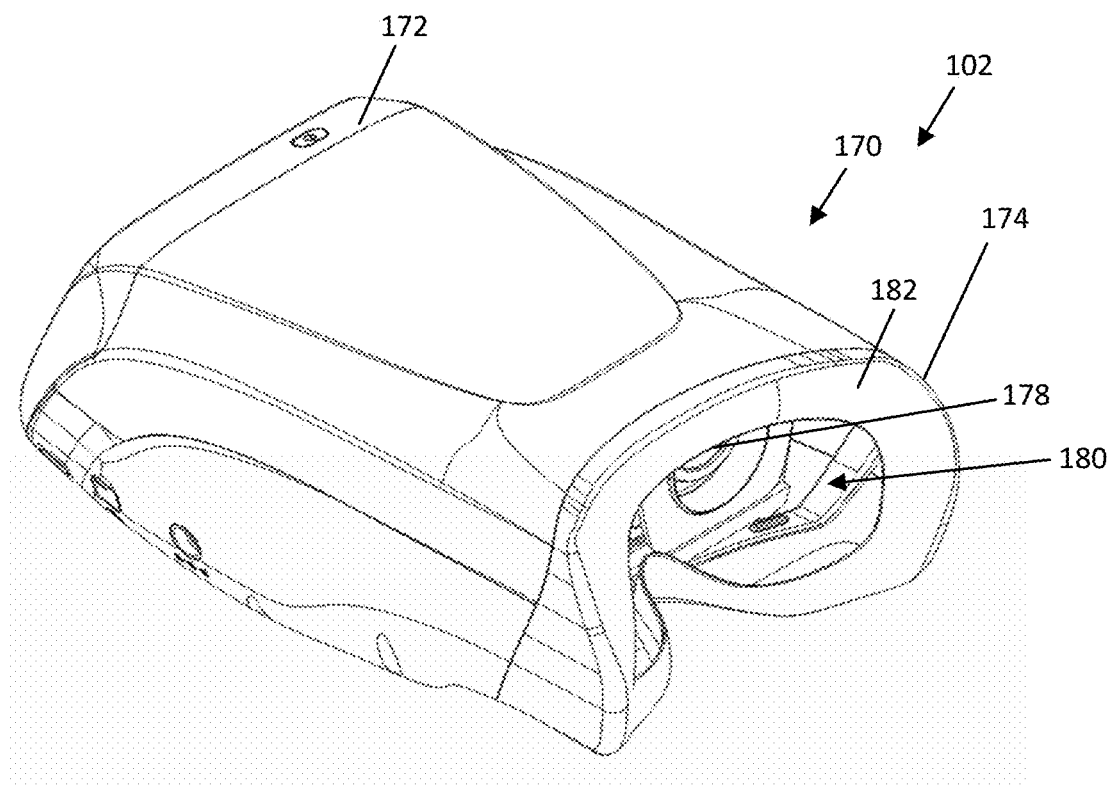
FIG. 5 is another view of the fundus imaging device of FIG. 4.
Figure 6:
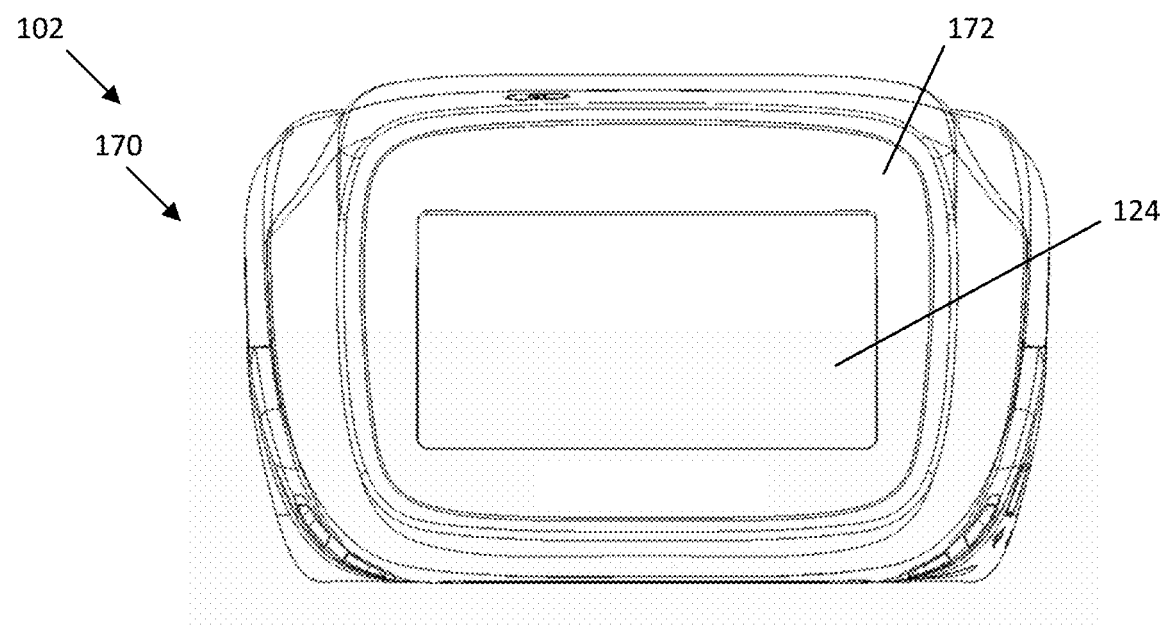
FIG. 6 is another view of the fundus imaging device of FIG. 4.
Figure 7:
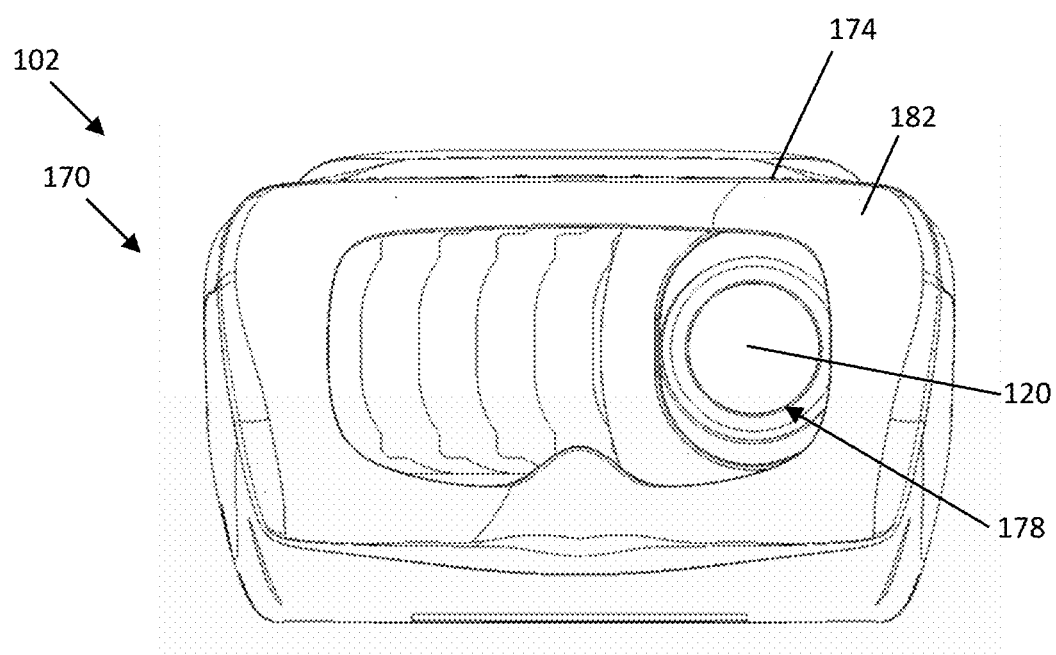
FIG. 7 is another view of the fundus imaging device of FIG. 4.

As shown in FIGS. 5 and 7, the housing 170 includes apertures 178 for imaging one or two eyes at a time. The camera 120 of the fundus imaging device 102 is positioned within a cavity 180 formed at the end 174 of the housing 170. In certain examples, the housing 170 supports structure for raising and lowering the camera 120 to align it with the patient's P eyes. The camera 120 can be moved in three directions to accomplish imaging of both eyes of the patient P as the housing 170 is positioned against the patient P's head.

The housing 170 supports positional guides for the patient P such as a surface 182 on the opposite end 174 of the housing 170 that is configured to engage the patient P's head. In certain embodiments, the housing 170 may also support additional positional guides such as an optional adjustable chin rest. The surface 182 is configured to be positioned against the patient P's head and to surround both eyes of the patient P. When the fundus imaging device 102 is used by the patient P to capture one or more images of their eyes, such as for example without the help or assistance of the clinician C, the positional guides such as the surface 182 may help the patient P align their eyes with the one or two apertures 178.

In the example embodiment shown in FIGS. 4-7, the housing 170 supports the display 124. In certain embodiments, the system 100 can also use a secondary display that is part of a smart phone, tablet computer, or external monitor separately located from the housing 170 to display the at least one image captured by the camera 120.

The display 124 functions to reproduce the images produced by the fundus imaging device 102 in a size and format that are readable by a clinician C. For example, the display 124 can be a liquid crystal display (LCD) and active matrix organic light emitting diode (AMOLED) display. The display 124 can be touch sensitive.

The housing 170 of the example fundus imaging device 102 is sized to be handheld. The display 124 can display images of the eye and controls for capturing those images. In some embodiments, the display 124 is a touchscreen. In some embodiments, the housing 170 additionally supports one or more user input buttons near the display 124. The display 124 and user input buttons can be used to capture one or more images of the patient P's eyes. Thus, the fundus imaging device 102 is capable of being configured such that the clinician C can implement one or more automatic and/or manual workflows to capture images of the patient P's eyes.

Additionally, the fundus imaging device 102 can be configured to automatically perform workflows to capture one or more images of the patient P's eyes without requiring the patient P or clinician C to use the display 124 or the one or more user input buttons near display 124 to control the operation of the fundus imaging device 102. Such configuration is helpful when the fundus imaging device 102 is used by the patient P without assistance from the clinician C such as when the eye imaging device 102 is used to monitor the progression of a contagious disease such as a coronavirus (e.g., COVID-19) to reduce exposure to the clinician C and other caregivers within an acute care space such as an intensive care unit of a hospital.

The fundus imaging device 102 can detect when the patient's P eyes are aligned with the one or two apertures 178 at the end 174 of the housing 170, such that the patient P is positioned and ready for the image capture sequence. In certain embodiments, the camera 120 of the fundus imaging device 102 can detect when the patient P's eyes are aligned with the one or two apertures 178.

Figure 8:
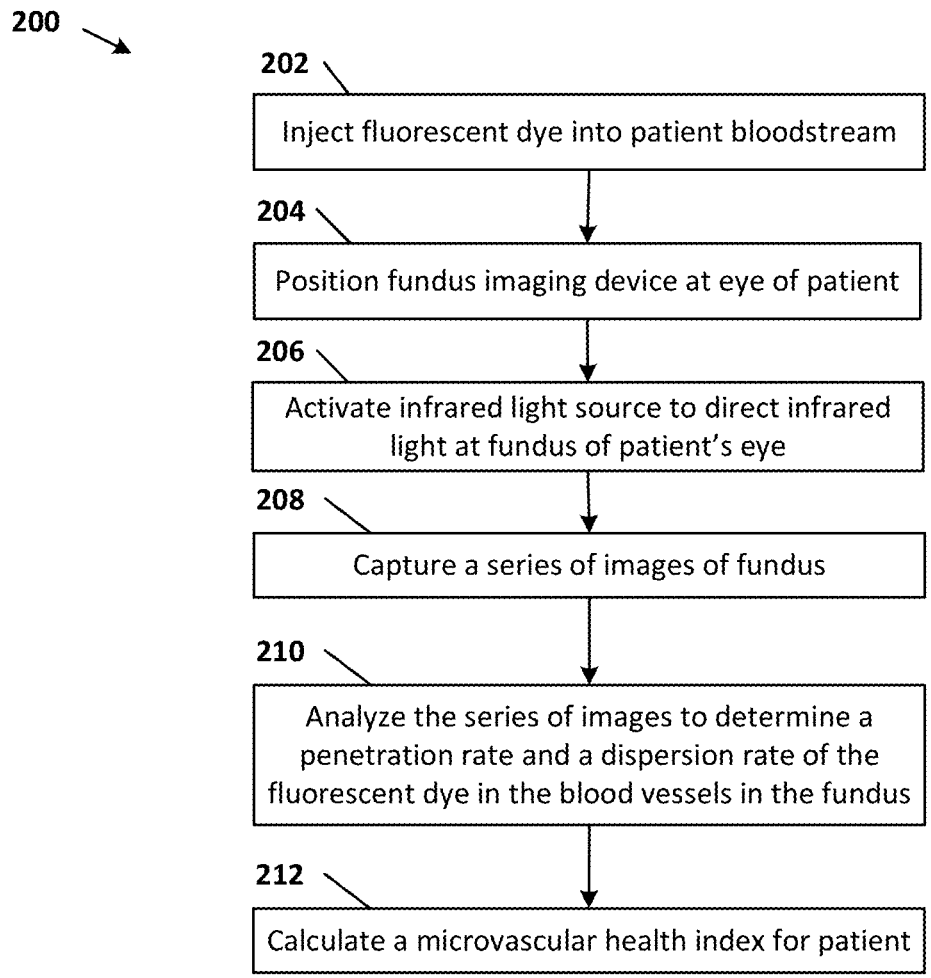
FIG. 8 is a flow diagram of an example method of assessing microvasculature of a patient.

FIG. 8 is a flow diagram of an example method 200 of assessing microvasculature of a patient. In particular, this method 200 utilizes fluorescent dye to image blood flow in microvessels of the patient's eye. In some embodiments, the method 200 is performed by the system 100 described in FIGS. 1-3.

At operation 202, fluorescent dye is injected into the patient's bloodstream. In some embodiments, the fluorescent dye is fluorescein. Fluorescein is a fluorophore having peak excitation at 494 nm and peak emission at 521 nm. When exposed to infrared light, fluorescein emits light of a bright yellowish green color.

At operation 204, a fundus imaging device is positioned at the patient's eye. In some embodiments, the fundus imaging device 102 of FIG. 1 is utilized. In some embodiments, color bandpass filtering is implemented on the fundus imaging device 102. The bandpass filter is selected to allow the yellowish green light to pass through, but filter out all other light.

At operation 206, an infrared LED source of the fundus imaging device is activated to direct infrared light at a fundus of the patient's eye. In some embodiments, the infrared light excites the fluorescent dye, causing it to emit a yellowish green light.

At operation 208, a series of images of the patient's fundus are captured. The images include microvessels that are illuminated as the fluorescent dye is pumped through the patient's blood vessels and into the fundus. As the patient's heart continues to beat, the fluorescent dye is pumped back out of the fundus and the yellow illumination fades away. In some embodiments, the series of images are recorded by the camera 120 of the fundus imaging device 102.

At operation 210, the series of images is analyzed to determine a penetration rate and a dispersion rate of the fluorescent dye in the blood vessels in the fundus. In some embodiments, the images are analyzed by the image processor 150 of the microvascular assessment computing device 104. In some embodiments, the penetration rate and dispersion rate are determined with an image processing algorithm based on the how the number of yellow and green pixels changes over time. These rates are affected by the patient's microvascular health. If the amount of fluorescent dye detected in the blood vessels does not reach a minimum threshold or if the fluorescent dye takes a long time to enter the blood vessels in the fundus, this could indicate an underlying health problem that is affecting the patient's endothelial health.

At operation 212, a microvascular health index is calculated for the patient. In some embodiments, the microvascular health index calculator 152 performs this step based on the penetration rate and dispersion rate determined in operation 210. The microvascular health index indicates to a clinician C when a patient P may need additional medical attention or diagnostic testing.

Figure 9:
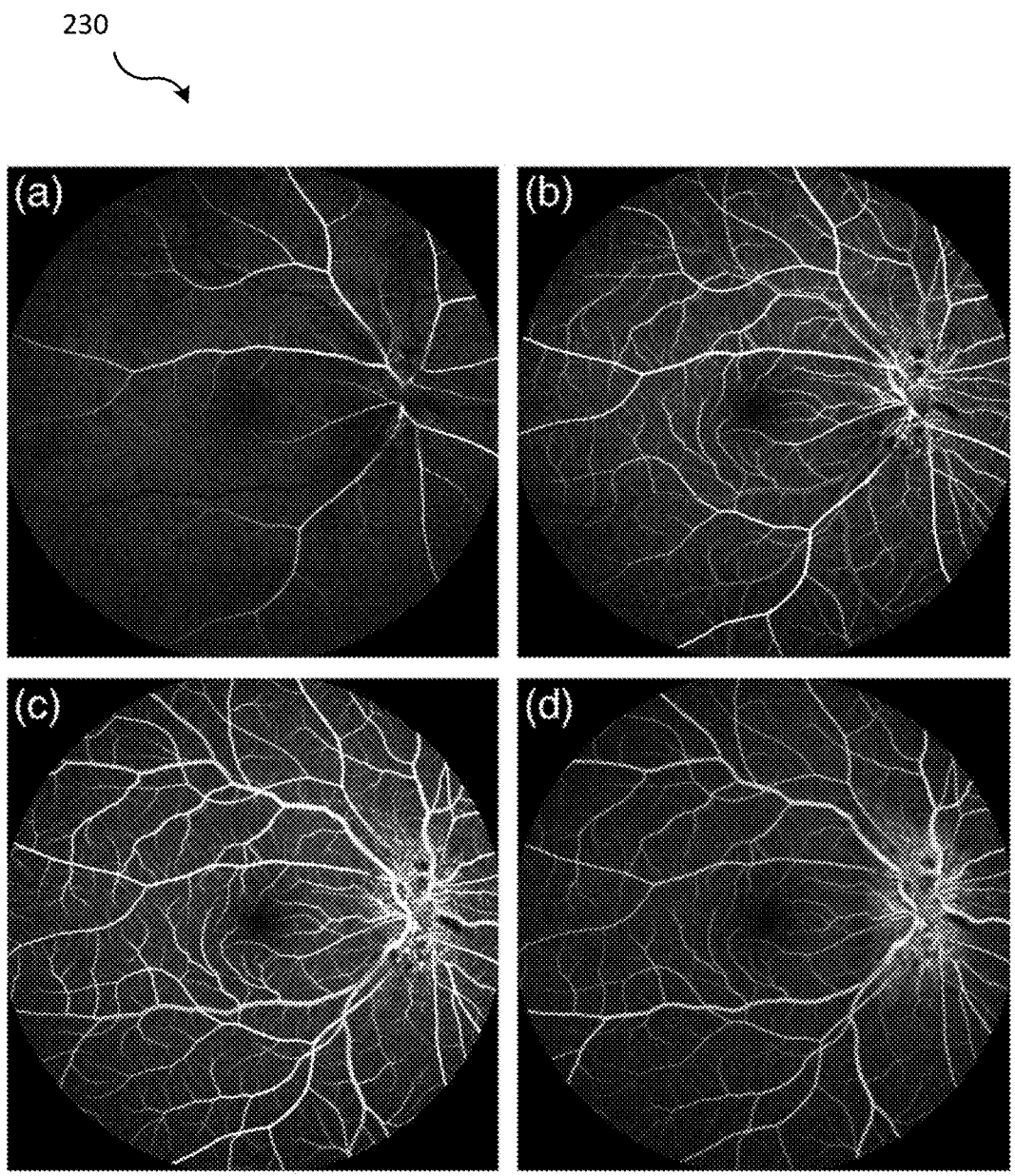
FIG. 9 illustrates a series of example images taken using the method of FIG. 8.

FIG. 9 illustrates a series 230 of example images taken using the method of FIG. 8. Panel (a) shows the fluorescent dye beginning to penetrate the small blood vessels of the fundus. In panel (b) the fluorescent dye has penetrated the majority of the blood vessels. In panel (c) peak levels of fluorescent dye are recorded in the fundus. In panel (d) the fluorescent dye has begun to disperse from the blood vessels. Overall, the level of fluorescence detected in the fundus should increase and then decrease such that if the levels were plotted in a graph, the graph would create a curve.

FIG. 10 is a flow diagram of another example method 250 of assessing microvasculature of a patient. In particular, this method 250 analyzes a fundus image to quantify a density of vessels in the microvasculature of a patient's eye. In some embodiments, the method 200 is performed by the system 100 described in FIGS. 1-3.

At operation 252, a fundus imaging device is positioned at the patient's eye. In some embodiments, the fundus imaging device 102 of FIG. 1 is utilized. In some embodiments, a wide field of view is selected for capturing the image.

At operation 254, the image of the fundus is captured. In some embodiments, the patient's eye is illuminated with infrared or near-infrared light to eliminate the effect of light exposure on the pupil so that a wide field of view can be captured. In some embodiments, a lower level of visual light illumination is utilized to capture the image to allow for a wider field of view.

In some embodiments, a longer exposure time may be needed to properly image the fundus with low levels of illumination. In such embodiments, due to the dynamic nature of the task (eye movement), multiple captured frames are stitched together with an algorithm. The algorithm registers the retina. The images are re-oriented and aligned to a common centroid point. The multiple images are binned to increased the dynamic range and fidelity with lowering the noise floor.

In some embodiments, near dark imaging of the fundus is employed. Sensitivity enhancement DQE utilizes an actively cooled CMOS, SIPM/SPAD imager. Bounds are set on the flux levels desired. This is used in combination with a patient LUT to determine the thermal load necessary for the imager to reach the sensitivity and DQE for proper imaging.

At operation 256, the image of the fundus is manipulated to localize edges of the blood vessels in the patient's fundus. In some embodiments, an algorithm is employed to modify the image to enable identification of branches in blood vessels. The image contrast is expanded. A color thresholding technique is used to highlight major blood vessels. Successive morphological eroding and dilating is used to localize edges of the blood vessels.

At operation 258, blood vessels are traced from a primary artery to determine branching point locations of the blood vessels. Atlas based anatomy is used to find root nodes which are identified for primary artery and vein structures. A genetic snake algorithm is rooted at a primary artery and venous location tracing the blood vessel tree structure. Along each path of the structure, branching points are enumerated where the left or right edge is lost along the tree generated by the snake algorithm.

At operation 260, diameters of the blood vessels are calculated both before and after each branching point location. Using branching point locations and the known photogrammetry of the imaging device, a diameter is measured to interpret vessel width.

At operation 262, distances between the branching point locations are measured. Distances are measured between successive branching point locations.

At operation 264, ratios of diameters of the branching point locations and the distances between the branching point locations are calculated. For each calculation, the diameter of the branching location to the distance along the tree to the next (or prior) branch is computed. In some embodiments, central retinal vein equivalent diameter (CRVE) and central retinal artery equivalent diameter (CRAE) are segmented from the visible image using a localized atlas based segmentation computation. Ultimately, a final score metric is calculated for the ratio diameter of vessel to number of branches on a single path.

At operation 266, clinical characteristics of the patient are determined based on the calculated ratios. The ratios are used to determine an absolute metric of vessel shunting and correlates to clinical characteristics.

In some embodiments, following operation 264, the field of view is adjusted to localize the minor descendants of the primary blood vessel at the extremes of the oculus. Another iteration of the operations 256, 258, 260, 262, and 264 can be performed.

Figure 11:
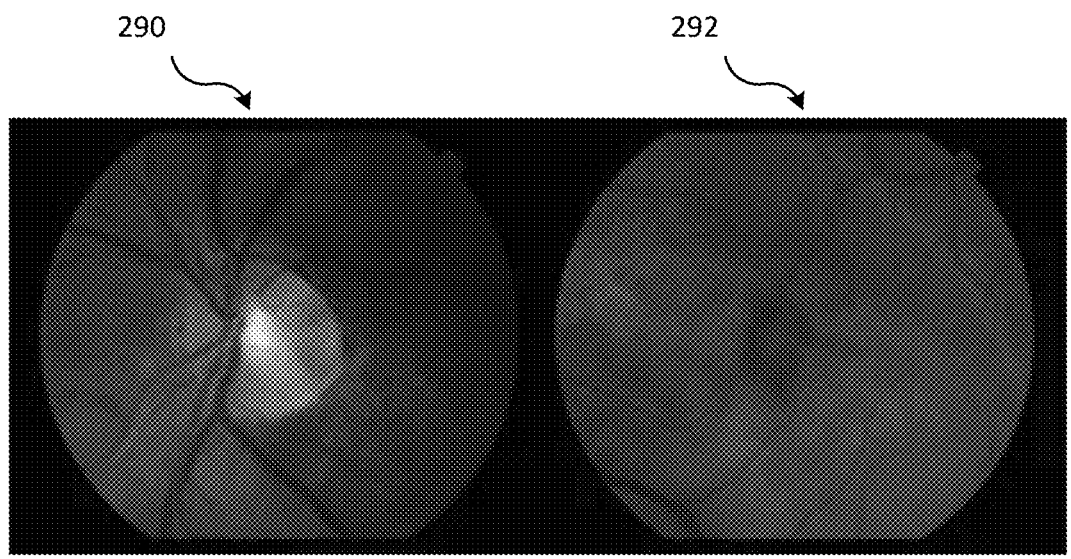
FIG. 11 illustrates an example of two different fundus images.

FIG. 11 illustrates an example of two different fundus images. The left fundus image 290 shows a greater number of branches than the right fundus image 292. Therefore, the ratios of the two images will be very different.

Figure 12:
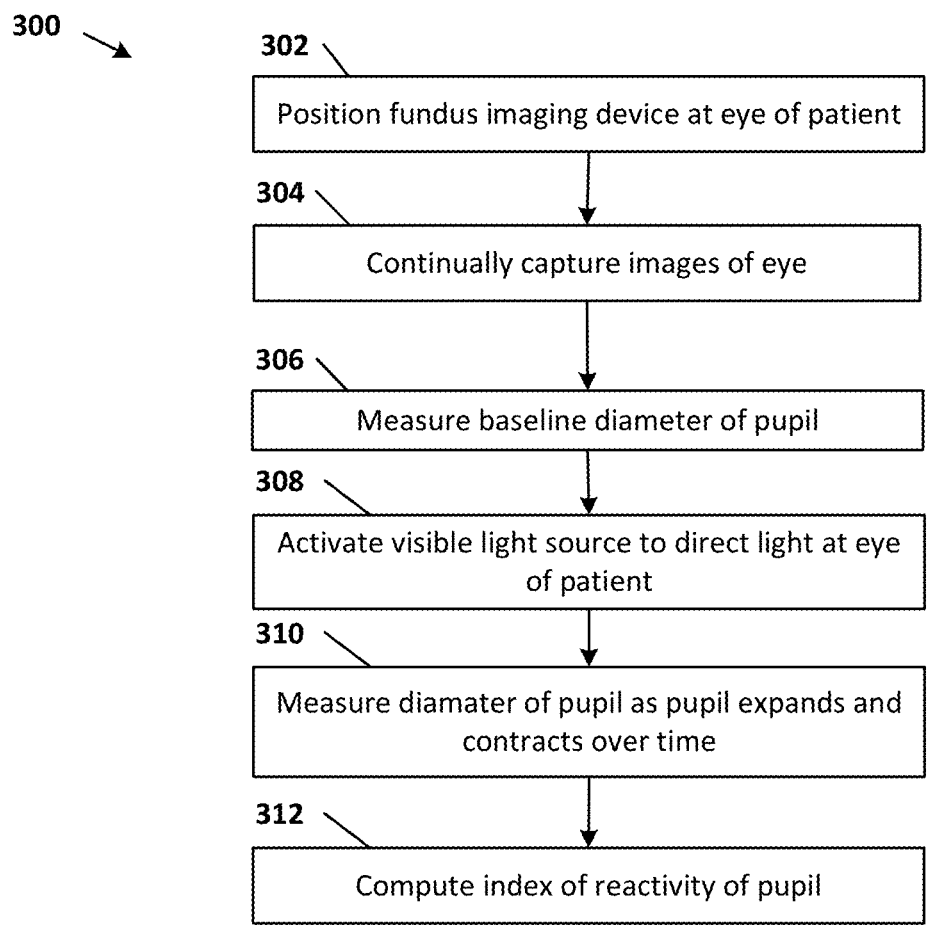
FIG. 12 is a flow diagram of another example method of assessing microvasculature of a patient.

FIG. 12 is a flow diagram of another example method 300 of assessing microvasculature of a patient. In particular, the method 300 measures the response of a patient's pupil to light stimulus. The rate of contraction of the pupil can be a meaningful metric for the overall health of the patient. In some embodiments, the method 300 is performed by one or more components of the system 100 of FIGS. 1-3.

At operation 302, a fundus imaging device is positioned at an eye of the patient. The fundus imaging device includes at least a camera and a visible light source. In some embodiments, the fundus imaging device is the fundus imaging device 102 of FIG. 1.

At operation 304, images are continually captured of the eye. In some embodiments, a camera captures images at a frequency of about 100 frames per second.

At operation 306, a baseline diameter of the pupil in the images is measured. This measurement is taken at a steady state with low ambient lighting. In some embodiments, this step is performed by the image processor 150 of FIG. 3.

At operation 308, the visible light source is activated to direct light at the eye of the patient. The light causes the patient's pupil to contract. At operation 310, the diameter of the pupil is measured as it expands and contracts over time.

In one embodiment, the visible light source is activated to provide a brief flash of light. The diameter of the pupil is measured continuously as the pupil contracts in response to the light. Measurements continue to be taken after the light stops until the pupil begins to expand again. This is called edge threshold detection.

In another embodiment, the visible light source is activated to slowly increase in brightness. A-priori targets are selected for starting and end diameters of the pupils. The quantity of illumination flux required to generate a pupil contraction response is measured. This metric is used to determine sensitivity of the pupil.

Returning to operation 312, an index of reactivity of the pupil is computed. Acceleration, velocity, and peak values of pupil diameter are used to compute the index of reactivity. In some embodiments, this step is performed by the pupil reactivity calculator 154 of FIG. 3. The index of reactivity can be used by clinicians to determine a general level of health of a patient.

Additional methods of evaluating microvascular health and endothelial health are also possible with the fundus imaging device 102. In one example, a method of assessing microvasculature of a patient involves fundus image capture synchronized with QRS waveform data. Blood vessels mechanically deform as a response to pressure and flow rate changes of blood. Interstitial time to peak flow change will result in an expansion and contraction of the vessel. This elasticity can be measured as a function of the flow rate.

A fundus imaging device is positioned at an eye of the patient. A camera of the fundus imaging device operates to continually capture images of the eye of the patient. At the same time that fundus imaging is occurring, several heartbeat cycles of the patient are recorded. In some embodiments, the heartbeats are recorded with an echocardiogram machine (ECG). QRS waveform data is used to synchronize the fundus images with the heartbeat cycles. Post-acquisition analysis is conducted. Image segmentation and vessel identification is performed. Correlated differential imaging is used to subtract the peak vessel diameter from the minimum vessel diameter based on the heartbeat pattern, in a number of locations along the fenestration of the imaged microvasculature. Coaxial vessel movement is also measured at registration points using a similar approach. These measures are then used to compute a compliance factor for the patient that is representative of the clinical condition of the endothelium.

In another example, cell measurements are taken of endothelial cells lining the cornea to directly evaluate endothelial health of a patient. A different imaging plane and task is combined with the fundus imaging device. This is used to image individual cells of the cornea endothelial layer. These images are then used to compute a ratio of damages cells to healthy cells. A fundus imaging device is positioned at an eye of the patient. The fundus imaging device is modified to include a camera having polarization filtering, dark field illumination, and a high magnification factor. Images of individual endothelial cells lining a cornea of the eye are captured. A ratio of damaged endothelial cells to healthy endothelial cells is calculated. This ratio can be informative to a clinician in determining a state of endothelial health for the patient.

Figure 13:
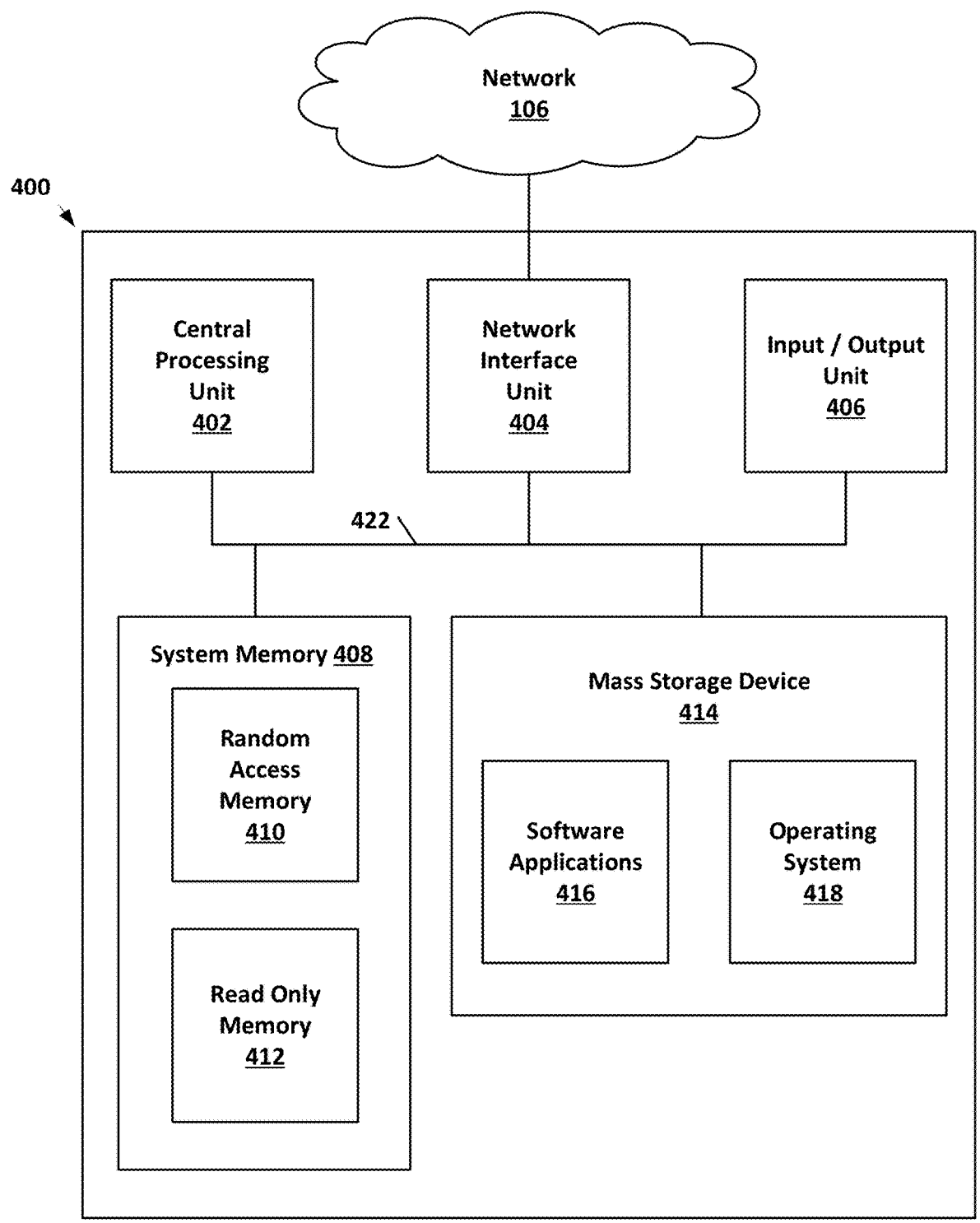
FIG. 13 is a schematic block diagram of an example computing device usable to implement aspects of the fall risk management system of FIG. 1.

FIG. 13 is a block diagram illustrating an example of the physical components of a computing device 400. The computing device 400 could be any computing device utilized in conjunction with the system 100 for microvascular assessment of a patient, such as the computing device 122 of FIG. 2.

In the example shown in FIG. 13, the computing device 400 includes at least one central processing unit ("CPU") 402, a system memory 408, and a system bus 422 that couples the system memory 408 to the CPU 402. The system memory 408 includes a random access memory ("RAM") 410 and a read-only memory ("ROM") 412. A basic input/output system that contains the basic routines that help to transfer information between elements within the computing device 400, such as during startup, is stored in the ROM 412. The computing device 400 further includes a mass storage device 414. The mass storage device 414 is able to store software instructions and data.

The mass storage device 414 is connected to the CPU 402 through a mass storage controller (not shown) connected to the system bus 422. The mass storage device 414 and its associated computer-readable storage media provide non-volatile, non-transitory data storage for the computing device 400. Although the description of computer-readable storage media contained herein refers to a mass storage device, such as a hard disk or solid state disk, it should be appreciated by those skilled in the art that computer-readable data storage media can include any available tangible, physical device or article of manufacture from which the CPU 402 can read data and/or instructions. In certain embodiments, the computer-readable storage media comprises entirely non-transitory media.

Computer-readable storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the computing device 400.

According to various embodiments, the computing device 400 can operate in a networked environment using logical connections to remote network devices through a network 421, such as a wireless network, the Internet, or another type of network. The computing device 400 may connect to the network 421 through a network interface unit 404 connected to the system bus 422. It should be appreciated that the network interface unit 404 may also be utilized to connect to other types of networks and remote computing systems. The computing device 400 also includes an input/output controller 406 for receiving and processing input from a number of other devices, including a touch user interface display screen, or another type of input device. Similarly, the input/output controller 406 may provide output to a touch user interface display screen or other type of output device.

As mentioned briefly above, the mass storage device 414 and the RAM 410 of the computing device 400 can store software instructions and data. The software instructions include an operating system 418 suitable for controlling the operation of the computing device 400. The mass storage device 414 and/or the RAM 410 also store software instructions, that when executed by the CPU 402, cause the computing device 400 to provide the functionality discussed in this document. For example, the mass storage device 414 and/or the RAM 410 can store software instructions that, when executed by the CPU 402, cause the computing device 400 to control operation of the camera 120.

Although various embodiments are described herein, those of ordinary skill in the art will understand that many modifications may be made thereto within the scope of the present disclosure. Accordingly, it is not intended that the scope of the disclosure in any way be limited by the examples provided.

What is claimed is:

1. A system for microvascular assessment of a patient, the system comprising:
   a fundus imaging device comprising:
      a camera configured to capture one or more images of an eye of the patient; and
      at least one light source; and
   a microvascular assessment computing device comprising:
      a processor; and
      memory encoding instructions which, when executed by the processor, cause the system to:
         activate the light source to direct light at a fundus of the eye of the patient;
         capture, with the camera, one or more images of the fundus of the patient, the fundus comprising a plurality of blood vessels;
         analyze, with the microvascular assessment computing device, the one or more images to determine a penetration rate and a dispersion rate of a fluorescent dye in the blood vessels in the fundus; and
         determine, based on the penetration rate and the dispersion rate, a microvasculature health index for the patient.

2. The system of claim 1, wherein the at least one light source is an infrared light emitting diode.

3. The system of claim 1, wherein the memory further encodes instructions, which, when executed by the processor, cause the system to measure a diameter of a pupil of the patient.

4. The system of claim 1, wherein the memory further encodes instructions, which, when executed by the processor, cause the system to:
   manipulate the one or more images of the fundus to localize edges of blood vessels in the fundus;
   trace the blood vessels from a primary artery to determine branching point locations of the blood vessels;

calculate diameters of the blood vessels before and after each branching point location;

determine distances between each branching point location; and compute ratios of the diameters of the branching point locations and the distances between the branching point locations.

5. The system of claim 1, further comprising a color bandpass filter.

6. The system of claim 1, further comprising a polarization filter.

* * * * *